(12) United States Patent
Gunn et al.

(10) Patent No.: US 8,524,258 B2
(45) Date of Patent: Sep. 3, 2013

(54) STRUCTURED LOTIONS

(75) Inventors: Euen T. Gunn, Trenton, NJ (US); Glenn A. Nystrand, Lebanon, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 505 days.

(21) Appl. No.: 12/340,858

(22) Filed: Dec. 22, 2008

(65) Prior Publication Data
US 2010/0158961 A1 Jun. 24, 2010

(51) Int. Cl.
*A61K 8/02* (2006.01)

(52) U.S. Cl.
USPC ........................................................ 424/401

(58) Field of Classification Search
USPC ........................................................ 424/401
See application file for complete search history.

(56) References Cited

U.S. PATENT DOCUMENTS

| | | | |
|---|---|---|---|
| 4,711,776 A * | 12/1987 | Suzuki et al. | 424/70.28 |
| 4,879,116 A * | 11/1989 | Fox et al. | 424/682 |
| 5,182,373 A | 1/1993 | Kim | |
| 5,888,489 A * | 3/1999 | von Mallek | 424/70.19 |
| 6,017,548 A | 1/2000 | Epstein et al. | |
| 6,528,070 B1 * | 3/2003 | Bratescu et al. | 424/401 |
| 6,919,074 B2 | 7/2005 | Milbradt | |
| 7,074,395 B2 * | 7/2006 | Milbradt et al. | 424/70.1 |
| 7,150,883 B2 | 12/2006 | Killer | |
| 2004/0076654 A1 | 4/2004 | Vinson et al. | |
| 2009/0005449 A1 | 1/2009 | Gunn | |
| 2009/0005460 A1 | 1/2009 | Gunn | |

FOREIGN PATENT DOCUMENTS

| | | |
|---|---|---|
| WO | WO 97/00623 | 6/1996 |
| WO | WO 00/54749 A1 | 3/2000 |

OTHER PUBLICATIONS

Baydar et al. International J. of Cosmetic Science 13(4) 169-190 (1991).*
www.chemicalland21.com/specialtychem/perchem/DISTEARYLDIMONIUM%20CHLORIDE.htm (2006).*
Bernheim-Grosswasser, S., et al. "Spherulites: A New Vesicular System with Promising Applications. An example: Enzyme Microencapsulation", J. Chem. Phys. 112 7 (2000), pp. 3224-3430.
Diat, O., et al. "Preparation of Monodisperse Multiplayer Vesicles of Controlled Size and High Encapsulation Ration", J. Phys. II France 3 1 (1993), p. 9-14.
Diat, O., et al. "Effect of Shear on a Lyotropic Lamellar Phase", J. Phys. II France 3 9 (1993), pp. 1427-1452.
Freund, O., et al. "In Vitro and in Vivo Stability of New Multilamellar Vesicles", Life Sci. 67 (2000), pp. 411-419.
Fukushima, S., et al. "Preparation of and Drug Release from w/o/w Type Double Emulsions Containing Anticancer Agents", Chem. Pharm. Bull. 31 11 (1983), pp. 4048-4056.
Garti, A., et al. "Mechanistic Considerations on the Release of Electrolytes from Multiple Emulsions Stabilized by BSA and Non Ionic Surfactant", J. Controlled Release 29 (1994), pp. 41-51.
Gauffre, F., et al. "Evidence for a pH Difference Controlled by Thermodynamics between the Interior and the Exterior of a New Type of Vesicles in Suspension", Langmuir, 15 (9) (1999) pp. 3070-3077.
Grossiord, J., et al. "Significance of Rheological Analysis in Studies of W/O/W Multiple Emulsions", Rheol. Acta 32 (1993), pp. 168-180.
Grossiord, J., et al. W/O/W Multiple Emulsions: A Review of the Release Mechanisms by Break-Up of the Oily Membrane, S.T.P. Pharma Sciences 11 (2001) pp. 331-339.
Hamilton, R.T., et al. "Alkali Metal Ion Transport Through Thin Bilayers", J. Phys. Chem. 94 (1990), pp. 2560-2566.
Jager-Lezer, N., et al. "Influence of Lipophilic Surfactant on the Release Kinetics of Water-Soluble Molecules Entrapped in a w/o/w/ Multiple Emulsion", J. Controlled Release 45 (1997), pp. 1-13.
Oliveri, L., et al. "Study of the Breakup Under Shear of a New Thermally Reversible Water-in-Oil-in Water (W/O/W) Multiple Emulsion", Pharm. Res. 18 5 (2001), pp. 689-693.
Pays, K., et al. "Double Emulsions: How Does Release Occur?" J. Controlled Release 79 (2002), pp. 193-205.
Roux, D, et al. "Rheology of Lyotropic Lamellar Phases", Europhys. Lett. 24 1 (1993), pp. 53-58.
Silva Cunha, J., et al. "W/O/W Multiple Emulsion of Insulin Containing a Protease Inhibitor and an Absorption Enhancer: Preparation, Characterization and Determination of Stability Towards Proteases in Vitro", Int. J. Pharm. 158 (1997), pp. 78-89.
Tedajo, G., et al. "pH Compartmented w/o/w Multiple Emulsion: A Diffusion Study", J. Controlled Release 75 (2001), pp. 45-53.
Yoshioka, J., et al. "Prolonged Release of Bleomycin from Parenteral Gelatin Sphere-in-oil-in Water Multiple Emulsion", Chem. Pharm. Bull. 30 4 (1982), pp. 1408-1415.

* cited by examiner

*Primary Examiner* — Shirley V Gembeh

(57) ABSTRACT

Provided are structured compositions comprising a quaternary ammonium salt, at least one branched fatty alcohol, and a vehicle.

17 Claims, No Drawings

STRUCTURED LOTIONS

FIELD OF INVENTION

The present invention relates to self-assembling, structured compositions, and uses of such compositions in personal care products.

DESCRIPTION OF THE RELATED ART

A variety of so-called "structured" compositions for use in personal care, home care, and other consumer products are known in the art. Such structured compositions are often typified by the presence of a lamellar, surfactant-rich phase, and tend to exhibit desirable rheological and aesthetic properties, as well as, significant power to suspend functional ingredients that are not soluble in water.

Unfortunately, the vast majority of structured systems require high levels of shear in order to form the structured composition. This is unfortunate, since this adds additional process and scale-up difficulties as well as additional expense in order to form these compositions.

Accordingly, Applicants have recognized that, it would be desirable to develop structured compositions that are thermodynamically stable or "self-assembling." While "self-assembling" structured compositions are known, they can be difficult to form and conventional self-assembling structured compositions are limited to very specific chemistries. For example, U.S. Pat. No. 7,150,883 to Keller et al. describe a composition with one or more diacylglycerol-PEG lipids, that is useful for preparing liposomal formulations. However, PEG-derivatives have various drawbacks, e.g., the need to utilize ethylene oxide feedstocks and limited substantivity to body surfaces.

In light of the above, Applicants have recognized the need to develop new self-assembling structured compositions, and methods of making and using such compositions.

SUMMARY OF THE INVENTION

The present invention meets the aforementioned need and overcomes the disadvantages of the prior art. In particular, applicants have discovered that at least one quaternary ammonium salt having the structure below, can be combined with at least one branched fatty alcohol and a vehicle to produce self-assembling structured compositions.

The quaternary ammonium salt is defined by the following structure:

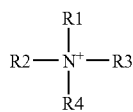

Wherein R1, R2, R3 and R4 are pendant groups each comprising at least one carbon bonded to the nitrogen, and at least two of R1, R2, R3, and/or R4 comprise hydrophobic moieties comprising at least seven carbon atoms.

According to one aspect, the present invention provides a structured composition comprising the quaternary ammonium salt defined above, at least one branched fatty alcohol, and a vehicle. The structured composition has a yield stress from about 1 Pascal (Pa) to about 10,000 Pa.

According to another aspect, the present invention provides methods of treating the skin comprising topically applying a structured composition comprising a quaternary ammonium salt defined above, at least one branched fatty alcohol, and a vehicle. The structured composition has a yield stress from about 1 Pascal (Pa) to about 10,000 Pa.

DESCRIPTION OF PREFERRED EMBODIMENTS

All percentages listed in this specification are percentages by weight, unless otherwise specifically mentioned.

As used herein the term "structured composition," means a composition having a Yield Stress from about 1 Pascal (Pa) to about 10,000 Pa as measured via the "Yield Stress Test" described in the Test Methods below. Examples of certain preferred structured compositions include those having a Yield Stress of from about 1 Pa to about 1500 Pa, and, more preferably those having a Yield Stress of from about 10 Pa to about 1100 Pa, as measured by the Yield Stress Method described hereafter.

As used herein the term "self-assembling structured composition" means a structured composition that is thermodynamically stable at ambient conditions, e.g., 25° Celsius. Little or no energy need be added when mixing the components of the composition in order to form a phase-stable structured composition.

In certain preferred embodiments, the structured composition includes one or more lamellar phases distributed in an exterior phase. By "lamellar phase" it is meant sheet-like structures of hydrophobic moieties essentially sandwiched between hydrophilic moieties. The sheet like structures may be flat or take on curvature. In certain preferred embodiments, the lamella take on curvature and form enclosed structures or vesicles. The vesicle may be essentially spherulitic, i.e., such as spherulites. In certain other embodiments, the lamella arrange themselves into "multilamellar vesicles," a series of enclosed structures that are concentric or otherwise enclose one another. In other embodiments, the composition may include "worm-like" structures which are essentially structures that are "hybrid" between lamellar sheets and spherulites.

As noted above, applicants have discovered unexpectedly that structured compositions, particularly ones including vesicles, and more particularly self-assembling vesicles may be obtained by combining at least one quaternary ammonium salt having the structure define above, at least one branched fatty alcohol, and a vehicle. Applicants have further discovered that compositions of the instant invention, according to certain embodiments have the desirable attribute of forming vesicles, and, in particular, multi-lamellar an/or spherulitic vesicles, and, in particular self-assembling vesicles. This is especially advantageous in that little to no energy of mixing is required to create these structures.

Applicants have further unexpectedly discovered that benefit agents can be added to the composition and the benefit agents can associate with the lamella or vesicles, thereby rendering the composition more stable.

Any of a variety of suitable quaternary ammonium salts may be used in the compositions of the present invention. By "quaternary ammonium salt," it is meant an amine having a quaternized nitrogen that has been substituted with at least one hydrophobic moiety. By "hydrophobic moiety" it is meant any nonpolar, generally water-insoluble groups containing seven or more carbon atoms. Certain preferred hydrophobic moieties include moieties comprising about eight or more carbon atoms, more preferably about ten or more carbon atoms, even more preferably at least about twelve carbon atoms, and most preferably 14 or more carbon atoms. The carbon atoms may be arranged in an uninterrupted fashion (e.g., each of the carbon atoms other than those terminating the particular group of carbon atoms have neighboring carbon atoms). Nonlimiting examples of hydrophobic groups include any alkyl, aryl or arylalkyl group, e.g., saturated or unsaturated linear, branched, cyclic, or aromatic hydrocarbon species. Functionalities that may be included in the hydrophobic group are, for example, ether, ester, ketone, amide, carbonate, urethane, carbamate, or xanthate functionalities. In one preferred embodiment, the hydrophobic moiety includes an alkyl group having seven or more carbon atoms, preferably 10 or more carbon atoms, and even more preferably 12 or more carbon atoms, and most preferably 14 or more carbon atoms.

In general, quaternary ammonium salts have a permanent, pH independent charge. One skilled in the art will recognize that this pH independent charge behavior is in contrast to primary ammonium cations ($RNH_3^+$), secondary ammonium cations ($R_2NH_2^+$) and tertiary ammonium cations ($R_3NH^+$). Suitable quaternary ammonium salts include those of the formula:

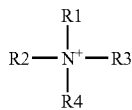

wherein each of R1, R2, R3, and R4 are pendant groups having at least one carbon atom bonded to the $N^+$ and at least two of R1, R2, R3, and R4 comprise hydrophobic groups having at least seven carbon atoms.

In the structure above, $N^+$ is a quarternized nitrogen. Quaternary ammonium salts useful in the present invention have at least two of R1, R2, R3, and R4 that are or include hydrophobic moieties having at least seven carbon atoms; the remainder of the R1, R2, R3, and R4 are "substituted" (i.e., do not each consist only of a hydrogen atom) but do not do not include hydrophobic moieties having at least seven carbon atoms. As such, the remainder of the R1, R2, R3, and R4 may be, for example, selected from the following: methyl, ethyl, or hydroxyl groups. In a preferred embodiment, the remainder of the R1, R2, R3, and R4 are methyl groups.

In a preferred embodiment, exactly two of R1, R2, R3, and R4 include hydrophobic moieties having at least seven carbon atoms. For example, R2 and R3 may each be hydrophobic moieties. In one embodiment of such, the hydrophobic moieties having at least seven carbon atoms in R2 and R3 are identical. In yet another embodiment, R2 and R3 have different carbon chain lengths. For example, R2 may have a carbon chain length that is at least 4, such as at least 6, such as at least 8 carbon atoms different that R3. In a less preferred embodiment, three or four of R1, R2, R3, or R4 include hydrophobic moieties having at least seven carbon atoms.

In certain preferred embodiments, two of R1, R2, R3, and R4 are independently selected from the group consisting of C7-C34 alkyl hydrophobic moieties, C7-C34 alkyl ester hydrophobic moieties, C7-C34 aralkyl hydrophobic moieties, C7-C34 amine/amido alkyl hydrophobic moieties and the other two of R1, R2, R3, and R4 are methyl, ethyl or hydroxyl, preferably methyl. In certain more preferred embodiments, two of R1, R2, R3, and R4 are independently selected from the group consisting of C7-C22 alkyl hydrophobic moieties, C7-C22 alkyl ester hydrophobic moieties, C7-C22 aralkyl hydrophobic moieties, C7-C22 amine/amido alkyl hydrophobic moieties and the other two of R1, R2, R3, and R4 are methyl, ethyl or hydroxyl, preferably methyl. In certain preferred embodiments, two of R1, R2, R3, and R4 are independently selected from the group consisting of C7-C18 alkyl hydrophobic moieties, C7-C18 alkyl ester hydrophobic moieties, C7-C18 aralkyl hydrophobic moieties, C7-C18 amine/amido alkyl hydrophobic moieties and the other two of R1, R2, R3, and R4 are methyl, ethyl or hydroxyl, preferably methyl.

In certain preferred embodiments, the quaternary ammonium salt is symmetrical. In certain preferred embodiments, the quaternary ammonium salt is assymmetrical.

In a preferred embodiment, the quaternary ammonium salt is a dialkyl ammonium compound, such as a dialkyl ammonium chlorides, such as distearyl ammonium chlorides, such as VARISOFT TA-100, commercially available from EVONIK Goldschmidt/Degussa GmbH of Essen, Germany. Other suitable quaternary ammonium compounds include "diester quats" that have two hydrophobic moieties, each of which include an alkyl group (tallow, palm oil, or rapeseed oil-derived) and an ester functional group. These are sold under the trade name STEPANTEX (e.g., STEPANTEX VK-90). Another suitable quaternary ammonium compound is a "diamidoamine quaternary" sold under the name ACCOSOFT. Another suitable quaternary ammonium compound is a "dialkyldimethyl ammonium chloride" sold under the name BTC (e.g., BTC 2125M). Yet another suitable quaternary ammonium compound is an arylalkyldimethyl ammonium chloride, such as an alkylbenzyldimethylammonium chloride sold under the trade name STEPANQUAT. STEPANTEX, ACCOSOFT, BTC and STEPANQUAT products are available from Stepan Company of Northfield, Ill.

The total concentration of quaternary ammonium salts meeting the particular structural requirements set forth above is preferably from about 0.1% to about 20% by weight of active quaternary ammonium salts in the composition, more preferably from 0.5% to about 10% by weight, even more preferably from about 1.0% to about 10%. By "total concentration of quaternary ammonium salt meeting the structural requirements set forth above" it is meant the all quaternary ammonium salts meeting the structural requirements set forth above are identified. The sum of the concentrations of each of these particular quaternary ammonium salts is then calculated.

Any of a variety of suitable branched fatty alcohols may be used in the present invention. By "branched fatty alcohol", it is meant, any of various alcohols derived from oils and fats (e.g., from plant or animal sources) or synthetic hydrophobic groups having at least one pendant hydrocarbon-comprising chain. The branched fatty alcohol may comprise any number of carbon atoms, such as from about 8 to about 34, preferably from about 7 to about 22 carbon atoms, more preferably about 9 to about 16 carbon atoms, and even more preferably about 11 to about 16 carbon atoms. Suitable branched fatty alcohols may comprise one or more alcohol groups per molecule. In certain preferred embodiments, the fatty alcohol comprises one alcohol group per molecule.

Suitable branched fatty alcohols may comprise one or more branches in the carbon backbone of the molecule. In certain preferred embodiments, the branched fatty alcohol is monobranched. By "monobranched", it is meant the fatty alcohol has an alkyl chain with one (CH) functional group resulting in one branch in the alkyl chain, i.e. the fatty alcohol has one and only one carbon that has one hydrogen atom and three carbon atoms bonded thereto.

In certain preferred embodiments, the branched fatty alcohol is a primary alcohol. By "primary alcohol," it is meant no —COH group is bonded to more than one carbon atom.

In one particularly preferred embodiment, the branched fatty alcohol is both monobranched and a primary alcohol. In a more particularly preferred embodiment, the branched fatty alcohol is both monobranched and a primary alcohol and has only one alcohol group per molecule.

In certain preferred embodiments, the branched fatty alcohol consists solely of hydrogen, carbon, and oxygen atoms. The carbon-carbon bonds within the branched fatty alcohol may be saturated or unsaturated.

In one particularly preferred embodiment, the branched fatty alcohol is a monobranched primary fatty alcohol that can be represented by the following structure (I):

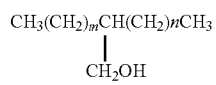

wherein: m+n=8 to 27 (inclusive); and m is an integer that ranges from 0 to 14 (inclusive); and n is an integer that ranges from 0 to 11 (inclusive).

Commercially available materials that are particularly suitable for use as the branched fatty alcohol include the following materials alone or in combination: Isalchem 123, Isofol 28, or Lialchem 123 produced by Sasol Chemical Co of Bad Homburg, Germany. In a particularly preferred embodiment, the branched fatty alcohol is Isofol 28, also known as "2-dodecylhexadecanol." Using the structural nomenclature (I) above, for 2-dodecylhexadecanol, m=14, n=11, m+n=25. Alternatively, 2-dodecylhexadecanol can be expressed as the structure (II) below where $R^1$ is C14H25, and $R^2$ is C12H25.

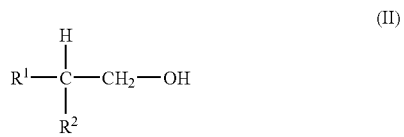

In one embodiment the branched fatty alcohol is a so-called "Guerber alcohol," i.e., an alcohol that is formed by converting a primary aliphatic alcohol into its β-alkylated dimer alcohol with loss of one equivalent of water. This may be particularly suitable for forming branched fatty alcohol from naturally derived fat or oil. One suitable example of a Guerber alcohol is Isofal 20 (octyl-2-dodeacnol) also available from Sasol. Using the structural nomenclature (I) above, for (octyl-2-dodeacnol), m=9, n=7, m+n=16. Alternatively, (octyl-2-dodeacnol) can be expressed using structure (II) for Isofol 28, except $R^1$ is C1OH25, and $R^2$ is C8H17.

In another embodiment, the branched fatty alcohol includes an alkoxylate moiety, such as ethoxy and/or propoxy groups. Any number of alkoxy groups are acceptable as long as the fatty alcohol is still capable of providing a structured composition. In one embodiment, the fatty alcohol has up to an including 10 alkoxy groups, more preferably from 0 to 3 alkoxy groups, most preferably from 1 to 3 alkoxy groups.

The total concentration of the branched fatty alcohols in the composition of the invention is preferably from about 0.1% to about 10% by weight of active branched fatty alcohol in the composition, more preferably from 0.1% to about 5% by weight, even more preferably from about 0.1% to about 3%. By "total concentration of branched fatty alcohols" it is meant the sum of the concentrations of all branched fatty alcohols present in the composition.

The quaternary ammonium salt and branched fatty alcohol may be present in the composition in a ratio of total quaternary ammonium salt to total branched fatty alcohol that is from about 1:1 to about 100:1, preferably from about 1.5:1 to about 50:1, more preferably from about 2:1 to about 25:1, most preferably from about 2:1 to about 10:1.

In one embodiment, to assist in the self-assembling of lamella, the composition includes an unbranched fatty alcohol or unbranched fatty acid. By "unbranched fatty alcohol or unbranched fatty acid", it is meant a fatty alcohol or fatty acid that has a linear structure, for example an aliphatic linear C8 to C34 alcohol, preferably C8 to C22, such as, for example, capryl, capric, lauryl, cetyl, stearyl, and the like. In one preferred embodiment, the carbon chain length of the unbranched fatty alcohol is no more than 4 carbon atoms less or more than the total carbon chain length of the branched fatty alcohol. In another embodiment, the carbon chain length of the unbranched fatty alcohol is no more than 4 carbon atoms less or more than the total carbon chain length of the branched fatty alcohol. In one particular embodiment, the unbranched fatty alcohol is cetyl alcohol.

The unbranched fatty alcohol and branched fatty alcohol may be present in the composition in a ratio of branched fatty alcohol to unbranched fatty alcohol that is from about 0.1:1 to about 100:1, preferably from about 0.1:1 to about 50:1, more preferably from about 0.1:1 to about 10:1, most preferably from about 1:1 to about 5:1.

The quaternary ammonium salt and the fatty alcohols described above are examples of amphiphilic compounds that are present in compositions of the present invention. By "amphiphilic compounds" it is meant those compounds having both one or more hydrophobic moieties and one or more hydrophilic moieties. By hydrophilic moiety it is meant any anionic, cationic, zwitterionic, or nonionic group that is polar and generally water-soluble. Nonlimiting examples include anionics such as sulfate, sulfonate, carboxylic acid/carboxylate, phosphate, phosphonates; cationics such as: amino, ammonium, including mono-, di-, and trialkylammonium species, pyridinium, imidazolinium, amidinium, poly(ethyleneiminium); zwitterionics such as ammonioalkylsulfonate, ammonioalkylcarboxylate, amphoacetate; and nonionics such as hydroxyl, sulfonyl, poly(ethyleneoxy), amido, ureido.

Each of the various amphiphilic compounds present in compositions of the present invention have a theoretical packing parameter associated therewith. $P_a$ is the theoretical packing parameter with respect to surface and $P_v$ is theoretical packing parameter with respect to volume (D D Lasic, Liposomes: From Physics to Applications, Elsevier, pp 51, 1993). The parameters are derived from the equations $HC_a/T_a = P_a$ and $HC_v/T_v = P_v$, where $HC_a$ is the hydrocarbon chain area, $T_a$ is the total area of the molecule, $HC_v$ is the volume of the hydrocarbon chain and $T_v$ is the volume of the whole molecule. Theoretical packing parameter for a particular amphiphilic compounds can be determined using appropriate computer software, such as Molecular Modeling Pro v. 6.1.1, available from Chem S W of Fairfield, Calif.

In one embodiment the theoretical packing parameter of the quaternary ammonium salt suitable for use in the present invention is greater than about 0.5, preferably greater than about 1.0, more preferably from about 1.0 to about 2.0, most preferably from about 1.25 to about 2.0.

Theoertical packing parameters of the inventive composition as a whole, $P_{a,\ composition}$ can also be calculated, as a weighted average of the individual theoertical packing parameters, $P_a$ for each the amphiphiles (preferably just the amphiphiles that have a hydrophobic moiety having an uninterrupted carbon chain length of at least about 8, and more preferably at least about 12 carbon atoms) present in the inventive composition. Specifically, since ideal mixing of these compounds results in arithmetic average of their individual characteristics. For instance $HC_d/T_a = P_a$ of a binary mixture, in the case of ideal mixing can be expressed as a weighted average, specifically: $<P_a> = X_1 P_1 + X_2 P_2$, $X_1 + X_2 = 1$. More generally in the case of more than two of such amphiphilic compounds, in a given composition can be represented by: $<P_a> = \Sigma_i X_i P_i$ and $\Sigma_i X_i = 1$ where $X_i$ is the mole fraction of the amphiphile in the mixture and $P_i$ is the packing parameter with respect to surface of that lipid. In one embodiment, in order to facilitate the formation of spherulites in the composition, the theoretical packing parameter, $P_{a, composition}$, is from about 0.5 to about 1.0.

In one embodiment, the composition includes a humectant that serves to enhance spreadibility and/or moisture retention. Any of a variety of commercially available humectants, which are capable of providing moisturization and conditioning properties to the personal cleansing composition, are suitable for use in the present invention. Examples of suitable humectants nonexclusively include: 1) water soluble liquid polyols selected from the group comprising glycerine, propylene glycol (e.g., 1-2 or 1-3 propanediol), hexylene glycol, butylene glycol, dipropylene glycol, polyglycerols, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof. In A preferred embodiment, the humectant is preferably a polyhydric alcohol such as glycerol or a propanediol such as propylene glycol. The humectant may be present in an amount of from about 1% to about 70% by weight in composition, more preferably from about 1% to about 40% by weight, even more preferably from about 5% to about 30%, and most preferably from about 10% to about 25%, based on the overall weight of the composition.

In one embodiment, the composition includes a hydrophobic compounds or emollients that may serve to provide increase spreadibility and/or provide moisture retention to the skin or hair. The hydrophobic compounds may be, for example, any of a variety of hydrophobic materials that are either liquid or solid at room temperature, has a carbon or silicon-oxygen chain length of at least about 3, more preferably at least about 5, and are capable of spreading across the skin and forming a film thereon, when used in a composition of the present invention. Examples of suitable water-insoluble hydrophobic compounds include, but are not limited to emollients such as oils including mineral oils, petrolatum, vegetable or animal-derived oils (triglycerides and the like.); non-hydrocarbon based oils such as dimethicone, and other silicone oils as well as silicone gums; waxes including polyethylene waxes, and other mixtures of fatty esters (e.g., isopropyl myrsitate or isopropyl palmitate and the like), not necessarily esters of glycerol and the like. The concentration of the hydrophobic compound in the composition of the invention (alone or in combination) is preferably from about 1% to about 70% by weight in composition, more preferably from about 1% to about 40% by weight, even more preferably from about 1% to about 10%, and most preferably from about 10% to about 25%.

Compositions of the present invention include a vehicle. The vehicle is preferably a major constituent of an exterior phase in which the structured phase or phases (e.g., vesicles) are distributed or dispersed in a themodyamically favored manner. In one particularly preferred embodiment, the vehicle is a polar species such as water. The vehicle may be present in a concentration that is at least about 30%, preferably at least about 50%, more preferably at least about 60%, such as between about 60% and about 80%.

In order to reduce either (1) the potential for irritation, due to the composition not being rinsed from the skin, and/or (2) the potential for undesirable foaming, in certain embodiments, the composition of the present invention is substantially-free of one or more classes of ingredients. By "substantially free" it is meant that the composition includes less than about 1% of the particular ingredient class, preferably less than about 0.5%, more preferably less than about 0.1%. and even more preferably is completely free of such ingredients.

In one embodiment, the composition is substantially free of anionic surfactants. Anionic surfactants include branched or unbranched and may include alkyl olefin sulfonates, alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof.

In one embodiment, the composition is substantially free of amphoteric surfactants. Examples of amphoteric surfactants include, but are not limited to betaines as well as amphocarboxylates such as alkylamphoacetates (mono or di); phosphorylated imidazolines such as phosphobetaines and pyrophosphobetaines; carboxyalkyl alkyl polyamines; alkyliminodipropionates; alkylamphoglycinates (mono or di); alkylamphoproprionates (mono or di),); N-alkyl β-aminoproprionic acids; alkylpolyamino carboxylates; and mixtures thereof.

In one embodiment, the composition is substantially free of non-ionic surfactants. Examples of nonionic surfactants include, but are not limited to, fatty alcohol or amide ethoxylates, monoglyceride ethoxylates, sorbitan ester ethoxylates alkyl polyglycosides (condensation products of a long chain alcohol containing from about 6 to about 22 with glucose or a glucose-containing polymers); mixtures thereof, and the like.

While it may be desirable to limit or exclude non-ionic surfactants that would provide foam, it may be desirable to include non-ionic surfactants that have large hydrophilic groups, particularly if the concentration of electrolyte is high in the composition. As such, in certain embodiments, the composition includes electrolytes other than the quaternary ammonium salt and its counter ion. For example, the composition may include alkali metal cations, alkaline earth metal cations, transition metal cations, as well as any of various anionic species such as may perform various functions in the composition. The concentration of these electrolytes may be at least about 0.5% by weight, preferably at least about 0.75% by weight.

In order to stabilize the high level of electrolyte, certain non-ionic surfactants/emulsifiers may be included in the composition. Suitable nonionic emulsifiers include alkoxylated alcohols, polyglycerins, and polyglucosides. For example, nonionics with high HLBs (often referred to as "non-ionic O/W emulsifiers," even though they may not function as emulsifiers in the present composition), may enhance the packing of the quaternary ammonium compound and stabilize the electrolyte without creating foam. As such, in one embodiment, the composition may include the electrolyte described above and a non-ionic surfactant having an HLB (hydrophile-lipophile balance) of greater than about 13, preferably greater than about 14. Examples of suitable high HLB nonionic emulsifiers include alkoxylated fatty alcohols, such as polyethylene (or alternatively polypropylene) glycol ethers of fatty alcohols. One particularly suitable nonionic emulsifier is a polyethylene glycol ether of stearyl alcohol, such as steareth-21, which has an HLB of 16 and is available as BRIJ 721 from Uniquema of Chicago, Ill.

Alternatively, or preferably, in addition to the high HLB nonionic emulsifier, a low HLBs (often referred to as "non-ionic W/O emulsifiers," even though they may not function as emulsifiers in the present composition), as they may also enhance the packing of the quaternary ammonium compound without creating foam. As such, in one embodiment, the composition may include a non-ionic surfactant having an HLB (hydrophile-lipophile balance) of less than about 13, preferably less than about 12, more preferably less than about 10. One example of such a suitable nonionic emulsifier is a polyethylene glycol ether of stearyl alcohol, such as steareth-2, which has an HLB of 5 and is available as BRIJ 72 from Uniquema of Chicago, Ill.

By reducing or eliminating foaming surfactants such as those described above, one can formulate a lotion that can has the aesthetic attributes suitable, for example, a skin care lotion, or even a hair conditioner. As such, the composition may have a "Maximum Foam Volume" as determined by the "Foam Test" described below that is less than about 200 mL, preferably less than about 100 mL, more preferably less than about 50 mL, and even more preferably less than about 10 mL.

The following Foam Test is suitable to be performed on various personal care compositions to determine the Maximum Foam Volume upon agitation according to the present invention. The procedure is accomplished by adding 0.36 grams calcium chloride and 5.0 grams of the test product to 994.64 grams of deionized water and mixing until homogenous. The mixture is then added to a sample tank of a Sita R-2000 foam tester (commercially available from Future Digital Scientific, Co.; Bethpage, N.Y.). The test parameters are set to repeat three runs (series count=3) of 250 ml sample size (fill volume=250 ml) with nine stir cycles (stir count=9) for a 30 second stir time per cycle (stir time=30 seconds) with the rotor spinning at 1300 RPM (revolution=1300) at a temperature setting of 30° C.±2° C. Foam Volume data is collected at each stir cycle and the average and standard deviation of the three runs is determined. Maximum Foam Volume is reported for each Example as the value after the ninth stir cycle.

Compositions of the present invention may include a benefit agent. A benefit agent is any element, an ion, a compound (e.g., a synthetic compound or a compound isolated from a natural source) or other chemical moiety in solid (e.g. particulate), liquid, or gaseous state and compound that has a cosmetic or therapeutic effect on the skin, hair, mucosa, or teeth. As used herein, the term "benefit agent" includes any active ingredient such as a cosmetic or pharmaceutical, that is to be delivered into and/or onto the skin, hair, mucosa, or teeth at a desired location.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits such as, but not limited to: depigmentation agents; reflectants and optical modifiers; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; antiinfectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates and stress-reducing agents; antioxidants; hair lighteners; sunscreens; anti-edema agents, neo-collagen enhancers, anti-dandruff/sebhorreic dermatitis/psoriasis agents; keratolytics; lubricants; lightening and whitening agents; calcification, fluoridation and mineralization agents; and mixtures thereof.

In certain embodiments, the benefit agent included in the composition is either hydrophobic and/or susceptible to degradation by water. If the benefit agent is hydrophobic, it will generally associate with hydrophobic moieties of the lamella (or associate with vesicles if present). This is advantageous in that if the benefit agent is susceptible to degradation from water, the hydrophobic moieties of the lamella in the present invention serve to shield the benefit agent from degradation that would otherwise occur. For example, if the benefit agent was merely present in an emulsified oil phase of a conventional emulsion, degradation would be more likely or more severe.

In addition, by associating certain benefit agents with the vesicle, it is also possible in certain instances to mitigate irritation of particular benefit agents that tend, in high enough concentrations, to irritate the skin. One nonlimiting example of such a benefit agent that can irritate the skin is retinol. Those skilled in the art will recognize numerous other benefit agents that can irritate the skin.

Particularly suitable benefit agents include for example; e.g., alpha and beta hydroxyacids such as salicylic acid; retinoids such as retinol; amines such as N,N,N',N'-Tetrakis(2-hydroxypropyl)ethylenediamine (THPED), N,N,N',N'-Tetrakis(2-hydroxyethyl)ethylene diamine (THEED), N,N,N',N'-tetramethylethylene diamine (TEMED) (the structures of which are set forth below), enantiomers thereof, or salts and diastereoisomers thereof, such as those described in copending, commonly assigned published patent application, US20060193814, entitled, "Compositions for the treatment of signs of aging;" feverfew and extracts thereof, among other active ingredients.

The amount of the benefit agent that may be used may vary depending upon, for example, the ability of the benefit agent to penetrate through the skin, nail, mucosa, or teeth; the specific benefit agent chosen, the particular benefit desired, the sensitivity of the user to the benefit agent, the health condition, age, and skin and/or nail condition of the user, and the like. In sum, the benefit agent is used in a "safe and effective amount," which is an amount that is high enough to deliver a desired skin or nail benefit or to modify a certain condition to be treated, but is low enough to avoid serious side effects, at a reasonable risk to benefit ratio within the scope of sound medical judgment.

Compositions of the present invention may include other functional ingredients. In certain embodiments of the invention, compositions of the present invention include other functional ingredients. By other functional ingredients it is meant any moiety that serves one or more functions either to stabilize or provide aesthetic benefits to the composition or to impart one or more of various benefits to the end user. These various functional ingredients may be of any form at room temperature (e.g., solids, liquids, pastes and the like) and be dispersed, emulsified, or solubilized or otherwise homogenized within the composition.

A wide variety of functional ingredients may be used in compositions of the present invention, although it is preferred that the ingredient does not adversely affect the phase stability of the composition, and it is also preferred that the ingredient does not react prematurely with the depilatory active. By "adversely effect the phase stability," it is meant that by including the particular functional ingredient, when subject to a stability challenge (e.g., held at 22° C., 50% relative humidity for a week; when subject to three 48 hour freeze-thaw cycles) the composition irrevocably phase separates into two or more visually distinct phases so as to be displeasing (e.g., in a tactile, olfactory, and/or visual sense) for topical use.

Functional ingredients that may be used include, but are in no way limited to: such as, for example, salts such as sodium chloride to enhance viscosity; dyes and colorants; ultraviolet filters and sunscreens, opacificiers, matting agents, rheology modifiers; chelating and sequestering agents, pH adjusters, film forming polymers, and fragrance components; volatile silicones (polydimethylsiloxane, polydimethylcyclosiloxane, hexamethyldisiloxane, cyclomethicone fluids such as polydimethylcyclosiloxane), and preservatives (such as parabens, quaternary ammonium species, phenoxyethanol, benzoates, DMDM hydantoin).

It is typically unnecessary to include thickening agents in the composition (since the "thickening" is typically aesthetically and cost-effectively accomplished using the combination of anionic surfactant and the structuring agent, e.g., branched fatty alcohol). As such, compositions of the present invention may be substantially free of associative thickeners.

Examples of suitable thickening agents nonexclusively include: mono or diesters of 1) polyethylene glycol of formula: HO—(CH$_2$CH$_2$O)$_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); natural gums such as xanthan and guar gums; hydrophobically-modified ethoxylated urethanes (HEURs); hydrophobically-modified acrylic polymers, as well as, hydrophobically-modified cellulosics, hydrophobically-modified starches, combinations of two or more thereof, and the like.

Compositions of the present invention are structured, i.e., have a Yield Stress Yield Stress from about 1 Pascal (Pa) to about 10,000 Pa as measured via the "Yield Stress Test" described in the Test Methods below. Examples of certain preferred structured compositions include those having a Yield Stress of from about 1 Pa to about 1500 Pa, and, more preferably those having a Yield Stress of from about 10 Pa to about 1100 Pa, as measured by the Yield Stress Method, and preferably include a lamellar phase that is largely composed of one or more surfactants that is dispersed within an exterior (typically aqueous) phase. The viscosity of the personal care composition may be such that the composition is spreadable such as that of a cream or lotion or gel. For example, when measured using a LVT3 spindle at 30 rpm, the viscosity may be from about 500 cps to about 2000 cps.

The pH of the present compositions is not critical, but may be in a range that provides sufficient depilation, yet does not facilitate irritation to the skin, such as from about 5 to about 13, preferably from about 6 to about 8, and more preferably from about 6 to about 7.

In one embodiment of the present invention the structured composition comprises at least two visually distinct phases wherein a first phase is visually distinct from a second phase. Preferably, the visually distinct phases are packaged in physical contact with one another and are stable. Preferably, the visually distinct phases form a pattern such as stripes, ribbons, or striations. The ratio of a first phase to a second phase is typically from about 1:99 to about 99:1, preferably from 90:10 to about 10:90, more preferably about from 70:30 to about 30:70, still even more preferably about 50:50. As known in the art, the first visually distinct phase may include the components in a manner sufficient to provide structure, e,g, quaternary ammonium salt and branched fatty alcohol. The second visually distinct phase may also include the above-mentioned components in a manner sufficient to provide structure. Alternatively, the second phase may be unstructured.

Compositions of the present invention are typically extrudable or dispensable from a package, such as to be applied directly or indirectly, topically or orally to the body or another surface. Depending upon the particular function, compositions of present invention are desirably rubbed onto the skin and allowed to remain without rinsing. In another embodiment, the compositions of the present invention are rinse-off formulations, by which is meant the product is applied topically to the skin or hair, preferably the hair, and then subsequently (i.e., within minutes) the treated surfaces are rinsed with water.

Particularly suitable uses for compositions of the present invention include skin lotions, skin conditioners, and hair conditioners. Compositions of the present invention may also be used for stress-relief compositions (e.g., compositions with high concentrations of fragrant compounds), eye-treatment, oral care (e.g., toothpastes), among other personal care applications.

As discussed above, applicants have discovered unexpectedly that the instant methods provide personal care products having good aesthetics, such as excellent skin feel, body, and spreadiblity associated with the use of quaternary ammonium salts having pendant hydrophobic moieties. In addition, the compositions also surprisingly have the ability to form self-assembling lamellar phases without the need for high shear mixing. Furthermore, in certain embodiments the compositions may include a benefit agent and enhance the stability of the benefit agent so included.

The present invention provides methods of treating a body surface of the human body comprising contacting at least a portion of the body with a composition of the present invention. Certain preferred methods comprising contacting a body surface with a composition of the present invention to condition, moisturize, treat or prevent: signs of aging, acne, pigment contrast and pigmentation conditions, inflammation, redness, edema, dark circles, among other indications of the skin or muscosa; as well as caries prevention, plaque control and other indications of the teeth or oral cavity.

The present invention further provides methods of making a structured composition comprising combining, a particular quaternary ammonium salts described herein, a branched fatty alcohol, and a vehicle, and an optimal benefit agent, such as in a manner sufficient to achieve a composition having a Yield Stress of from about 1 Pa to about 10,000 Pa. For example, one may combine these by pouring, mixing, adding dropwise, pipetting, pumping, and the like, any one or more of such ingredients or compositions comprising such ingredients into any one or more of the other ingredients or compositions comprising such other ingredients in any order and optionally using any conventional equipment such as a mechanically stirred propeller, paddle, and the like.

The methods of the present invention may further comprise any of a variety of steps for mixing or introducing one or more of the optional components described hereinabove with or into the structured composition of the present invention either before, after, or simultaneously with the combining step described above. While in certain embodiments, the order of mixing is not critical, it is preferable, in other embodiments, to pre-blend certain components, such as the fragrance and the nonionic surfactant before adding such components into the structured composition.

EXAMPLES

The following Yield Stress Test is used in the instant methods and in the following Examples. In particular, as described above, the Yield Stress test is used to determine whether a composition is structured, according to the present invention.

Yield Stress Test:

The following Yield Stress Test is performed on various personal care compositions to determine the Yield Stress according to the present invention. Samples are placed in a water bath set at 25° C. for a period time sufficient to allow the sample to equilibrate (at least about an hour). The procedure is accomplished by gently placing about 1.0 grams of the composition to be tested was on the base plate of a properly calibrated rheometer (e.g., Advanced Rheometer AR 2000) having a 20 mm cone with a 1 degree angle, a 20 mm plate, a water bath, and a solvent trap. The sample size is just sufficient to allow some minor flow of the sample out of the gap once the final position of the cone and plate was reached (0.030 mm). To minimize shearing of the sample prior to testing, each sample is applied to the plate in a consistent manner, by gently scooping out the sample in one motion without significant shear or spreading, evenly layered on the plate, and without compressing and rotating the spatula away from the sample. The sample is centered on the base plate and laid relatively even across the plate. Once the measurement position is reached, a small bulge of the sample material protrudes from the gap. This is removed quickly and gently so as not to disturb the top plate and pre-shear the sample. [If the top plate was moved then the run is aborted.] The sample preparation described thus far is less than 20 seconds to reduce undue drying of the sample. The instrument was set for a controlled shear rate run (log) with a shear rate spanning from $0.01^{-1}$, to $300^{-1}$; 300 data points collected; 300 seconds test duration; 25° C. water bath. The output device attached to the rheometer is set to plot stress (Pa) as a function of shear rate $s^{-1}$. Yield stress is determined from the plot of yield stress versus shear rate as the stress at which the curve departs from linearity. The average and standard deviation of the 3 runs is determined.

Example Ex. 1

Preparation of Inventive Example

The inventive structured compositions of Example Ex. 1 was prepared by blending a particular ingredient with other ingredients according to the materials and amounts listed in Table 1:

TABLE 1

| Trade Name | INCI Name | Function | % wt. |
|---|---|---|---|
| Deionized Water | Water | Vehicle | 70.64 |
| Sodium Chloride | Sodium Chloride | Viscosity Increasing Agent | 0.01 |
| Colloidal Oat Flour | *Avena Sativa* (Oat) Kernal Flour | Skin Protectant | 1.00 |
| Snow White Petrolatum | Petrolatum | Emollient | 4.00 |
| Cetyl Alcohol | Cetyl Alcohol | Structuring Aid | 0.00 |
| Isofol 28 | Dodecylhexadecanol | Structuring Aid | 2.50 |
| Dow Corning Q7-9120 (20 CS) | Dimethicone | Emollient | 1.25 |
| Kessco IPP | Isopropyl Palmitate | Emollient | 3.00 |
| Varisoft TA-100 | Distearyldimonium Chloride | Structuring Aid | 5.00 |
| Glycerin | Glycerin | Humectant | 12.00 |
| Benzyl Alcohol | Benzyl Alcohol | Preservative | 0.60 |
| | | | 100.00 |

The structured compositions noted in Table 1 were prepared as follows: water was added to a process vessel. Mixing was begun and salt was added and mixed until dissolved. Oatmeal was sifted in and allowed to mix for about 5 minutes. Heat was applied and mixing continued until to 85 C. was reached. Glycerin was added and mixing continued while temperature was maintained at 85 C. Varisoft TA 100 was added, as was petrolatum and Isofol 28, DC Q7-9120 20 cs., and isopropyl palmitate. The composition was mixed at 85 C for another 10-15 minutes. The composition was then removed from heat and continued to mix and cooled. At 40 C, benzyl alcohol was added, q.s. with water and continue to mix and cool to 30-35 C. The composition was then filled into packaging.

Comparative Example Comp. 1

Preparation of Comparative Example

The comparative Example Comp. 1 was prepared by blending a particular ingredient with other ingredients according to the materials and amounts listed in Table 2:

TABLE 2

| Trade Name | INCI Name | Function | % wt. |
|---|---|---|---|
| Deionized Water | Water | Vehicle | 70.64 |
| Sodium Chloride | Sodium Chloride | Viscosity Increasing Agent | 0.01 |
| Colloidal Oat Flour | *Avena Sativa* (Oat) Kernal Flour | Skin Protectant | 1.00 |
| Snow White Petrolatum | Petrolatum | Emollient | 4.00 |
| Cetyl Alcohol | Cetyl Alcohol | Structuring Aid | 2.50 |
| Isofol 28 | Dodecylhexadecanol | Structuring Aid | 0.00 |
| Dow Corning Q7-9120 (20 CS) | Dimethicone | Emollient | 1.25 |
| Kessco IPP | Isopropyl Palmitate | Emollient | 3.00 |
| Varisoft TA-100 | Distearyldimonium Chloride | Structuring Aid | 5.00 |
| Glycerin | Glycerin | Humectant | 12.00 |
| Benzyl Alcohol | Benzyl Alcohol | Preservative | 0.60 |
| | | | 100.00 |

The composition noted in Table 2 was prepared in a manner similar to Example Ex. 1, except that cetyl alcohol was used in place of Isofol 28.

Example Ex. 2

Evaluation of Viscosity and Structure of Inventive Example and Comparative Example Samples of Ex. 1 and Comp. 1 were prepared. The viscosity of Ex. 1 and Comp. 1 were tested using a Brookfield viscometer (RVT, TD spindle, 10 rpm). Comp. 1 had a viscosity of 28,600 cps and Ex. 1 had a viscosity of 12,000 cps. This indicates that replacing the cetyl alcohol with branched fatty alcohol had a dramatic affect on rheology.

The formulation, Ex. 1 shown in Table 1 and Comparative Example, Comp. 1, shown in Table 2 were also evaluated for the presence and spacing of structures such as lamella or vesicles using Small Angle X-Ray Scattering (SAXS). A Hecus XRS Series I SAXS System was employed (available from Hecus X-Ray Systems GMBH of Graz, Austria). The SAXS system also included a Hiltonbrooks cabinet and generator, a Philips X-ray tube and tower, a Hecus modified Kratky camera system and a M Braun PSD and sample stage.

A sample of the inventive composition, Ex. 1 was injected into a 1 mm diameter quartz capillary (with a wall thickness of ~0.01 mm), the capillary being held in a cuvette. The cuvette was then placed in a temperature controlled sample stage, itself being mounted within a compact Kratky camera, which was subsequently evacuated (~0.4×10-1 mbar). A beam of Cu Kalpha X-rays (wavelength=1.514A, generated at 40 kV 30 mA) was passed through a collimation system that produced a horizontal X-ray beam ~40×0.5 mm which then traveled through the sample. Scatter from the sample was detected using a vertically mounted, gas-filled position sensitive detector, a 0.5 mm Ni filter being used to attenuate the primary beam. The scatter signal was collected over a period of about 600 seconds which gives a good signal-to-noise ratio.

The scan of Ex. 1 is consistent with the presence of structures having a bilayer spacing of 179 Angtroms. Furthermore, the amplitude of the scattered signal was consistent with a high degree of curvature, suggesting that it is likely that vesicles were present. However, the scan of Comp. 1 did not exhibit any evidence of vesicles.

Ex. 1 and Comp. 1 were also evaluated for the presence and spacing of structures such as lamella or vesicles using Freeze Fracture (Cryo) Scanning Electron Microscopy (SEM). The SEM images clearly indicate the presence of spherical structures (vesicles) having a diameter of approximately 179 Angstroms distributed within a continuous phase. However, the SEM images of Comp. 1 show no evidence of such vesicles.

Inventive Example Ex. 3

Preparation of Inventive Example and Evaluation of Presence of Retinol and Association of Retinol With Vesicles in Inventive Composition The formulations, Inventive Examples Ex. 3 and Ex. 4 shown respectively in Tables 3 and 4 below were prepared by blending a particular ingredient with other ingredients according to the materials and amounts listed in Tables 3 and 4. The formulations, Ex. 5-8, shown in Table 5, were formed by a process similar to that described above for Ex. 1. The samples were evaluated for the presence of retinol using UV-fluorescence. A Nikon Optiphoto-2 epi-fluorescent microscope with either UV-2A (excitation wavelength: 330-380 nm, emission wavelength: 420 nm) or DAPI filters (excitation wavelength: 360 nm, emission wavelength: 490-500 nm) was employed. A droplet (~10 uL) of test composition was smeared onto a glass slide and then covered with a cover glass. Both Inventive Examples Ex. 3 and Ex. 4 demonstrated a fluorescence signal when viewing with a UV-2A filter. However, only Inventive Example Ex. 3 demonstrated a fluorescence signal when viewed with a DAPI filter, indicating, as expected that Ex. 3, not Ex. 4 included retinol. Furthermore, the fluorescence image indicated that for Inventive Example Ex. 3, using the DAPPI filter, the fluorescence signal was present within structures that appear in the image as droplets. This is consistent with the conclusion that retinol was present within vesicles.

TABLE 3

| Inventive Example, Ex. 3 | | | |
|---|---|---|---|
| Trade Name | INCI Name | Function | % wt. |
| Deionized Water | Water | Vehicle | 70.55 |
| Snow White Petrolatum | Petrolatum | Emollient | 4.00 |

TABLE 3-continued

Inventive Example, Ex. 3

| Trade Name | INCI Name | Function | % wt. |
|---|---|---|---|
| Isofol 28 | Dodecylhexadecanol | Structuring Aid | 2.50 |
| Dow Corning Q7-9120 (20 CS) | Dimethicone | Skin Protectant | 1.25 |
| BHT | BHT | Anti-oxidant | 0.10 |
| Kessco IPP | Isopropyl Palmitate | Emollient | 3.00 |
| Varisoft TA-100 | Distearyldimonium Chloride | Structuring Aid | 5.00 |
| Glycerin | Glycerin | Humectant | 12.00 |
| Retinol 10S | *Glycine Soja* (Soybean) OIL and Retinol | Skin benefit agent | 1.00 |
| Benzyl Alcohol | Benzyl Alcohol | Preservative | 0.60 |
|  |  |  | 100.00 |

TABLE 4

Inventive Example, Ex. 4

| Trade Name | INCI Name | Function | % wt. |
|---|---|---|---|
| Deionized Water | Water | Vehicle | 71.55 |
| Snow White Petrolatum | Petrolatum | Emollient | 4.00 |
| Isofol 28 | Dodecylhexadecanol | Structuring Aid | 2.50 |
| Dow Corning Q7-9120 (20 CS) | Dimethicone | Skin Protectant | 1.25 |
| BHT | BHT | Anti-oxidant | 0.10 |
| Kessco IPP | Isopropyl Palmitate | Emollient | 3.00 |
| Varisoft TA-100 | Distearyldimonium Chloride | Structuring Aid | 5.00 |
| Glycerin | Glycerin | Humectant | 12.00 |
| Retinol 10S | *Glycine Soja* (Soybean) OIL and Retinol | Benefit agent | 0.00 |
| Benzyl Alcohol | Benzyl Alcohol | Preservative | 0.60 |
|  |  |  | 100.00 |

Example Ex. 4

Preparation of Inventive Examples

The inventive structured compositions of Example Ex. 5-8 were prepared by blending a particular ingredient with other ingredients according to the materials and amounts listed in Table 5:

TABLE 5

| Trade Name | INCI Name | Ex. 5 | Ex. 6 | Ex. 7 | Ex. 8 |
|---|---|---|---|---|---|
| Deionized Water | Water | 79.50 | 79.00 | 78.00 | 78.50 |
| Snow White Petrolatum | Petrolatum | 4.00 | 4.00 | 4.00 | 4.00 |
| Isofol 28 | Dodecylhexadecanol | 2.50 | 2.50 | 2.50 | 5.00 |
| Cetyl Alcohol | Cetyl Alcohol | 0.00 | 2.50 | 2.50 | 0.00 |
| Dow Corning Q7-9120 (20 CS) | Dimethicone | 1.25 | 1.25 | 1.25 | 1.25 |
| Kessco IPP | Isopropyl Palmitate | 3.00 | 3.00 | 3.00 | 3.00 |
| Varisoft TA-100 | Distearyldimonium Chloride | 5.00 | 5.00 | 5.00 | 5.00 |
| Glycerin | Glycerin | 2.00 | 0.00 | 0.00 | 0.00 |
| Brij 721 | Steareth-21 | 0.00 | 0.00 | 1.00 | 0.50 |
| Pursal HiPure P | Potassium Lactate | 1.00 | 1.00 | 1.00 | 1.00 |
| Neutrol TE | Tetrahydroxypropyl Ethylenediamine | 1.00 | 1.00 | 1.00 | 1.00 |
| Citric acid | Citric Acid | 0.15 | 0.15 | 0.15 | 0.15 |
| Benzyl Alcohol | Benzyl Alcohol | 0.60 | 0.60 | 0.60 | 0.60 |
|  |  | 100.00 | 100.00 | 100.00 | 100.00 |
|  | Phase separation @ time of manufacture | yes | yes | no | no |

The formulations, Ex. 5-8, shown in Table 5, were formed by a process similar to that described above for Ex. 1. Water was added to a process vessel and the temperature was set to 85 C. Mixing was begun and glycerin was added and mixed until dissolved. Varisoft TA 100 was added, as was petrolatum and Isofol 28, DC Q7-9120 20 cs., and isopropyl palmitate. The composition was mixed at 85 C for another 10-15 minutes. The composition was then removed from heat and continued to mix and cooled. At 45 C, benzyl alcohol as well as a pH 5-6 premix of potassium lactate, and nutrol and water were slowly added. Q.S. with water and continue to mix and cool to 30-35 C. It was noted whether the sample phase separated upon completion of the batch. Examples Ex. 5 and Ex. 6 maintained good physical stability without visual phase separation whereas Ex. 7 and Ex. 8 demonstrated visual phase instability (separation into two distinct layers) after storage for the same period. This suggests that for inventive structured lotions, when using high electrolyte levels, it is useful to include a non-ionic emulsifier having a large hydrophilic head group, such as steareth-21 to reduce the likelihood of phase separation.

The invention claimed is:

1. A structured composition comprising distearyldimonium chloride, 2-dodecylhexadecanol, at least one emollient, and a vehicle, wherein the structured composition has a yield stress from about 1 Pascal (Pa) to about 10,000 Pa.

2. The composition of claim 1 comprising from 0.5% to about 10% by weight of distearyldimonium chloride.

3. The composition of claim 2 comprising from 0.1% to about 10% by weight of 2-dodecylhexadecanol.

4. The composition of claim 1 wherein said at least one emollient comprises an emollient selected from the group consisting of mineral oils, petrolatum, vegetable oils, animal-derived oils, silicone oils, waxes, fatty esters, and combinations of two or more thereof.

5. The composition of claim 1 comprising from about 1% to about 70% by weight of emollient.

6. The composition of claim 1 further comprising at least one humectant.

7. The composition of claim 6 wherein said at least one humectant comprises a humectant selected from the group consisting of glycerin, propylene glycol, hexylene glycol, butylene glycol dipropylene glycol, polyglycerols, polyalkylene glycols of the formula: $HO-(R''O)_b-H$, wherein R'' is an alkylene group having from about 2 to about 3 carbon atoms and b is an integer of from about 2 to about 10, polyethylene glycol ethers of methyl glucose of the formula $CH_3-C_6H_{10}O_5-(OCH_2CH_2)_c-OH$, wherein c is an integer from about 5 to about 25, urea, and combinations of two or more thereof.

8. The composition of claim 1 comprising from about 1% to about 70% by weight of humectant.

9. The composition of claim 1 wherein said composition is free of one or both of anionic surfactants and amphoteric surfactants.

10. A structured composition comprising distearyldimonium chloride, 2-dodecylhexadecanol, at least one humectant, and a vehicle, wherein the structured composition comprises multilamellar vesicles.

11. The composition of claim 10 comprising from 0.5% to about 10% by weight of distearyldimonium chloride.

12. The composition of claim 11 comprising from 0.1% to about 10% by weight of 2-dodecylhexadecanol.

13. The composition of claim 12 wherein said at least one humectant comprises a humectant selected from the group consisting of glycerin, propylene glycol, hexylene glycol, butylene glycol dipropylene glycol, polyglycerols, polyalkylene glycols of the formula: $HO-(R''O)_b-H$, wherein R'' is an alkylene group having from about 2 to about 3 carbon atoms and b is an integer of from about 2 to about 10, polyethylene glycol ethers of methyl glucose of the formula $CH_3-C_6H_{10}O_5-(OCH_2CH_2)_c-OH$, wherein c is an integer from about 5 to about 25, urea, and combinations of two or more thereof.

14. The composition of claim 13 further comprising at least one emollient.

15. The composition of claim 14 wherein said at least one emollient comprises an emollient selected from the group consisting of mineral oils, petrolatum, vegetable oils, animal-derived oils, silicone oils, waxes, fatty esters, and combinations of two or more thereof.

16. The composition of claim 15 wherein said composition is substantially free of one or both of anionic surfactants and amphoteric surfactants.

17. The composition of claim 15 comprising from about 1% to about 70% by weight of emollient and from about 1% to about 70% by weight of humectant.

* * * * *